US008105820B2

(12) United States Patent
Brander et al.

(10) Patent No.: US 8,105,820 B2
(45) Date of Patent: Jan. 31, 2012

(54) ASSAY CHIP, AND USES OF SAID ASSAY CHIP TO DETERMINE MOLECULAR STRUCTURES AND FUNCTIONS

(75) Inventors: Karl Brander, Fulenbach (CH); Louis Tiefenauer, Doettingen (CH)

(73) Assignees: Paul Scherrer Institut, Villigen (CH); Leister Process Technologies, Sarnen (CH)

( * ) Notice: Subject to any disclaimer, the term of this patent is extended or adjusted under 35 U.S.C. 154(b) by 918 days.

(21) Appl. No.: 10/584,484

(22) PCT Filed: Nov. 15, 2004

(86) PCT No.: PCT/EP2004/012925
§ 371 (c)(1),
(2), (4) Date: May 7, 2007

(87) PCT Pub. No.: WO2005/064342
PCT Pub. Date: Jul. 14, 2005

(65) Prior Publication Data
US 2007/0275480 A1    Nov. 29, 2007

(30) Foreign Application Priority Data

Dec. 23, 2003  (EP) .................................... 03029726
Jan. 31, 2004  (EP) .................................... 04002119

(51) Int. Cl.
*C12M 3/00*   (2006.01)
(52) U.S. Cl. .................................................... 435/287.2
(58) Field of Classification Search .................... None
See application file for complete search history.

(56) References Cited

U.S. PATENT DOCUMENTS

| 5,716,526 | A  | * | 2/1998  | Kelemen et al. ............. 210/650 |
| 5,843,767 | A  | * | 12/1998 | Beattie ...................... 435/287.1 |
| 6,716,629 | B2 | * | 4/2004  | Hess et al. .................... 435/420 |
| 6,785,432 | B2 | * | 8/2004  | Letant et al. .................... 385/12 |
| 6,875,671 | B2 | * | 4/2005  | Faris ............................ 438/455 |
| 6,916,665 | B2 | * | 7/2005  | Bayley et al. ................ 436/149 |
| 7,060,507 | B2 | * | 6/2006  | Akeson et al. ............... 436/518 |
| 2002/0127585 | A1 | | 9/2002 | Nagasawa ......................... 435/6 |
| 2002/0191884 | A1 | * | 12/2002 | Letant et al. .................... 385/12 |
| 2003/0036204 | A1 | * | 2/2003  | Stark et al. .................... 436/172 |
| 2003/0066749 | A1 | * | 4/2003  | Golovchenko et al. .. 204/192.32 |
| 2003/0068639 | A1 | * | 4/2003  | Haneder et al. ................... 435/6 |
| 2003/0104512 | A1 | * | 6/2003  | Freeman et al. ................. 435/29 |
| 2003/0207326 | A1 | * | 11/2003 | Su et al. ......................... 435/7.1 |
| 2004/0120854 | A1 | * | 6/2004  | Heath et al. ..................... 422/57 |
| 2005/0230272 | A1 | * | 10/2005 | Lee et al. ........................ 205/792 |

FOREIGN PATENT DOCUMENTS
WO    WO 03/016040    *  2/2003

OTHER PUBLICATIONS

Celestino Padeste et al.; Modular Amperometric Immunosensor Devices; Transducers' 95. Eurosensors IX—the 8th international conference on solid state sensors and actuators, and eurosensors IX; vol. 2, Jun. 25-29, 1995, pp. 487-490; XP-010305158; Stockholm, Sweden.
L.X. Tiefenauer et al.; Bio-functionalized neurochips; Proceedings of the 23rd. annual international onference of the IEEE engineering in medicine and biology society. 2001 conference proceedings (EMBS). vol. 1 of 4, conf. 23, Oct. 25, 2001, pp. 733-736; XP-010593479; Istanbul, Turkey.
L.J. Heyderman et al.; "High volume fabrication of customised nanopore membrane chips"; Microelectronic engineering, Elsevier publishers BV.; vol. 67-68, Jun. 2003, pp. 208-213; XP-004428871; Amsterdam, Netherlands.
S. Kossek et al.; "Immobilization of streptavidin for immunosensors on nanostructured surfaces"; Journal of molecular recognition, Heyden&Son Ltd.; vol. 9, 1996, pp. 485-487, XP-000886890; London, Great Britain.
John J. Kasianowicz; "Nanometer-scale pores: Potential applications for analyte detection and DNA characterization"; vol. 18, No. 4, 2002, pp. 185-191, XP-009024573; Disease markers, Wiley, Chichester, Great Britain.
Thomas Kaasgaard et al.; "Lipid domain formation and ligand-receptor distribution in lipid bilayer membranes investigated by atomic force microscopy"; vol. 515, No. 1-3, Mar. 27, 2002, pp. 29-34, XP-004347736; FEBS letters, Elsevier science publishers, Amsterdam, Netherlands.

* cited by examiner

*Primary Examiner* — Ann Lam
(74) *Attorney, Agent, or Firm* — Laurence A. Greenberg; Werner H. Stemer; Ralph E. Locher

(57) ABSTRACT

An assay chip for investigation the functionality of membrane proteins and their interactions with molecules includes a nanopore array having a plurality of nanopores in a suitable support layer deposited on the nanopore substrate and being a substantially planar support layer having a plurality of nanopores corresponding to the nanopores of the nanopore substrate. The chip includes further a biologically effective layer capable to host at least a non-lipid molecule or functional molecule, deposited on the support layer and covering the plurality of nanopores, resulting in accesible nanopores from both sides of the biologically effective layer for measurement or imaging. The structured support allows generating a biologically effective membrane, such as a lipid bilayer membrane, having high and reliable stability in a manner that its fluidity is sustained in order to keep integrated membrane proteins in the lipid bilayer in its full biological functionality.

13 Claims, 4 Drawing Sheets

ASSAY CHIP, AND USES OF SAID ASSAY CHIP TO DETERMINE MOLECULAR STRUCTURES AND FUNCTIONS

BACKGROUND OF THE INVENTION

The invention relates to an assay chip for investigation of the functionality of membrane proteins and their interactions with molecules. Further, the invention relates to a process for analyzing the functionality of non-lipid molecules, such as a protein, being integrated in a fluid biological effective layer. Furthermore, the invention relates to the use of said assay chip.

Detailed knowledge about protein structures and their related functions is a key to understand molecular processes of life. Due to the powerful molecular cloning and gene expression technologies proteins for the purpose of analytical investigations can be produced in sufficient amounts. Proteomics is presently a very active field in life sciences research. The final aim is to achieve a comprehensive understanding of structure and function of proteins. This knowledge is a prerequisite for a rational design of new drugs. G-protein coupled receptors (GPCR) constitute the largest subgroup of cell membrane receptors and about half of them are considered to be targets for drugs. As for an example, the actual structure of bovine rhodopsin, a model for GPCR proteins, could recently be determined at a 2.8 Å resolution. GPCRs have a glycosylated N-terminal ligand binding site, seven trans-membrane helices and an intracellular G-protein binding domain. Ligand binding on the extracelluar part induces conformational changes in the trans-membrane helices bundle of the receptor protein resulting in a dissociation of the hetero-trimeric G-protein which is bound to the intracellular part of the GPCR into a α- and a βγ-subunit. G-protein are anchored covalently to the lipid bilayer and are currently classified in four families according to the nature of the α-subunits which interact with different target membrane proteins like enzymes or ion channels. After the dissociation of the G-protein the α-subunit laterally diffuse within the lipid bilayer and bind to the target protein and activate it.

Therefore, the composition and the fluidity of the lipid bilayer are in any type of functional analysis and screening process critical issues, especially of high interest when considering an economic process for screening purposes.

Arrays of immobilized GPCRs in micro-spots have recently been used to investigate compounds which specifically bind to this membrane protein. Such high throughput technologies allow a screening across or within receptor families and may be suitable for ligand fishing for orphan GPCRs. The biological response of the current about 140 orphan GPCR receptors are unknown which make it difficult to identity ligands as potentially useful drugs.

Deorphanization of non-olefactory GPCRs is currently a focus in the pharmaceutical industry and recently receptors with potential functions related to cancer and diabetes has been identified. The success in finding new binding compounds depends strongly on full functionality of the target protein as it is the case in the living cell. Allosteric sites on GPCRs which do not overlap with the binding sites for the natural agonist have a number of theoretical advantages over agonist binding sites for drugs such as saturability and high tissue specificity. Thus, allosteric sites are attractive targets sites for drugs which modulate receptor functions by increase or partially decreasing its activity. The binding of allosteric ligand or modulating proteins can result in membrane protein complexes consisting of several components. Again, for the investigation of such interactions highly sensitive functional assay systems are required in which the target membrane protein has to be fully mobile within the lipid bilayer membrane and well accessible.

In almost all cases of the in vitro assay systems as outlined below, biomembranes of unknown composition are immobilized on solid supports which often leads to a restricted fluidity of the lipid bilayer and a structural disturbance of the membrane protein. For that reason, these circumstances are greatly undesired in broad assay processing campagnes since for the drug screening processing the native functions of the proteins are potentially highly disturbed.

A second important class of membrane proteins are ion channels. The voltage-gated sodium channels of eukaryotes are complex membrane proteins composed of more than 2000 amino acids residues. The bacterial sodium channel is much simpler consisting of one-domain of 34 kD and it can be expressed at high rates and is therefore useful for assay technology development. High throughput screening assays use lipid bilayer membranes associated sensitive reporter molecules or fusion constructs consisting of the green fluorescence protein and the ion channel. By the use of the proposed highly sophisticated assay systems, a deeper insight into the function of membrane proteins of interest will be achieved. Both, academic research and drug discovery will profit from this knowledge.

Cell-based assays are well suited to monitor the biological response of GPCRs in their natural environment and are widely used to identify lead compounds in the drug discovery process. In order to understand molecular mechanisms, in vitro tests are required where the number of involved components is reduced. The functionality of membrane proteins in vivo depends on many factors: the composition of the lipid bilayer membrane, biological activation reactions such as phosphorylation or the intracellular $Ca^{++}$ concentration. The development of robust, functional biomimetic in vitro tests for membrane proteins is a demanding, highly interdisciplinary field. The first step is the reconstitution of the purified expressed recombinant proteins into lipid bilayer membranes, in order to bring them in the functional form. Vesicles consisting of lipid bilayers are commonly used to keep membrane proteins active in buffer solutions. Binding of ligands to proteins present in vesicles has been monitored when they are bound on sensor surfaces using surface plasmon resonance as the detection method. However, such vesicle preparations may require too high quantities of the protein to achieve a sufficiently high sensitivity in the measurements and they are not well suited to investigate many functional aspects. Therefore, several types of hybrid systems have been developed where planar lipid bilayer membranes are immobilized on solid supports.

Free standing membranes which span a hole in a Teflon support appear black. Such black lipid bilayer membranes are difficult to prepare and are extremely fragile since the lipid bilayer of 4 nm thickness has to span holes in the range of 200 μm to 1 mm. For research experiments, this limitation may be acceptable, however, for practical applications in the drug discovery stability of the assay system is a major issue. Therefore, since about 20 years techniques have been developed using supports in order to achieve a higher stability. Membrane proteins have been immobilized by fusion of lipid vesicles to supported lipid bilayers or directly to $SiO_2$. Planar bilayer formation from vesicle adsorbed to hydrophilic surfaces like mica could be visualized.

The changed physical properties of lipid bilayers when supported, however, strongly affect the function of the embedded membrane protein. In order to overcome these problems, lipid bilayer membranes have been immobilized on surfaces via tethers. The resulting cleft between the lipid bilayer membrane and the solid support mimics the intracellular space and the desired functionality of trans-membrane proteins is partially retained. Ligand binding to membrane proteins in the lipid bilayer has been monitored using fluorescence detection. Impedance was measured to determine the function of supported ion channels as well. The conductance of supported lipid bilayer membranes containing an iono-phore changes upon binding of ligands. This effect has been utilized to develop membrane protein based biosensors.

The advantages of a hybrid system are a gain in stability and the feasible preparation procedure. The formation of supported planar lipid bilayer membranes by fusion of vesicles with supported phospholipid monolayers has been established. For optical detection of ligand binding lipid bilayer membranes have been prepared on alkylated carboxylated dextrane polymer which has been immobilized on sensor surfaces in a high density. In a study using micropatterned surfaces it has been shown that hydrophilic-hydrophobic edges promote vesicle fusion. Furthermore, the fusogenic effects of short-chained alcohols, $Ca^{++}$-ions and PEG are known in the art. These studies show that vesicle composition, fusogenic agents, hydrophilicity, topographic and chemical properties of the surface and temperature are the most important factors influencing the formation of lipid bilayer membranes from vesicles adsorbed to solid supports.

Supported tethered lipid bilayer membranes as achieved according to the methods described above have also some major disadvantages. The composition of the fluid in the reservoir between the lipid bilayer membrane and the support can hardly be controlled and the fluidity of the immobilized lipid bilayer membrane is restricted. This constitutes a tremendous drawback since the functionality of membrane proteins is related to the fluidity of the lipid bilayer and their mobility therein. Additionally, the incorporation of membrane proteins with large trans-membrane loops—the acetylcholine receptor for instance has a 5 nm large intracellular part—are impeded since the intracellular space between the lipid bilayer and the support gained by a tether are too small for larger trans-membrane loops.

Furthermore, only one side of the tethered lipid bilayer membrane is accessible which makes it difficult to explore trans-membrane changes or transport of molecules. The non-native environment may result in an impairment of the functionality and in screenings physiological receptor functions may not be detected.

SUMMARY OF THE INVENTION

In the following the different membrane types like prepared lipid bilayers with a predefined composition, biomembranes of cellular origin and mostly unknown composition or functional layers of supramolecular assemblies are generally called biological effective layer.

It is therefore a specific aim of the invention to provide a device with a biological effective layer as a membrane having high and reliable stability in a manner that its fluidity is sustained in order to integrate a non-lipid molecule into said layer preserving its full biological functionality.

This aim will be achieved according to the invention by an assay chip for investigation of the functionality of non-lipid molecules and their interactions with molecules, comprising:
 a) a nanopore substrate having a plurality of nanopores;
 b) a suitable substantially planar support layer deposited on said nanopores substrate having a plurality of nanopores corresponding with said nanopore substrate;
 c) a biological effective layer being capable to host at least a non-lipid molecule or functional molecule, deposited on said support layer and covering the plurality of nanopores, resulting in accessible nanopores from both sides of the biological effective layer for measurements.

This assay chip offers an array of nanopores of macroscopic lateral dimension therefore providing both, supporting area to stabilize the biological effective layers (defined as a layer that preserves the full functionality of the non-lipid molecule hosted therein), such as a lipid bilayer membrane, and pores in a high density in which the biological effective layer remains fully fluid. This assay chip therefore offers a versatile system for various applications, like drug screening, functional protein analysis, toxicity analysis and the like. Due to the tiny thickness of the $Si_3N_4$-layer the respective $Si_3N_4$-membrane with the nanopores is also extremely thin and due to the applied fabrication technology these $Si_3N_4$-membranes are mechanically stable. The given aspect ratio of the pore diameter to thickness of the nanopore array allows an unimpeded diffusion of macromolecules to both, the lipid layer membrane and to the non-lipid molecule, such as membrane proteins, integrated therein. Further, the mechanically stabilized biological effective layer (that means the solid support layer being the $Si_3N_4$-membrane with the nanopores and the biological effective layer immobilized thereupon) offers free access from both sides of the biological effective layer what allows the investigation of complex interactions of molecules, such as natural ligands or the interaction with artificial effector molecules (such as drugs) with functional integrated membrane proteins and to elucidate the mechanism of signal transduction. Due to the accessibility from both sides, the transport of ions, molecules and particles through the biological effective layer by transporter proteins can be investigated in a micro-chamber system, i.e. in a two-compartment system. Surface patterning and microspotting technologies will allow to address specific nanopore arrays. Furthermore, the membrane proteins are sterically not impeded due to the preservation of their mobility and therefore can directly be investigated on their response to allosteric effects what is crucial for the development of new drugs with GCPRs as the target. The total surface area being nanostructured is in a range that on the one hand a sufficient amount of membrane protein molecules is present in order to enable the use of macroscopic methods for detection of a distinct binding by means of fluorescence or other sensitive detection methods. On the other hand the amount of precious membrane proteins and/or binding compounds is comparably low for the achievement of the desired screening process.

This assay chip with the nanostructured silicon nitride membrane supports the biological effective layer and thus bio-mimics the cytoskeleton.

Materials for a suitable support layer are silicon nitride ($Si_3N_4$) or silicon oxide ($SiO_2$) and the nanopore substrate is potentially of silicon and carbon containing materials but also a polymer, a metal, a dielectrica, a glass or a ceramic. Suitable is insofar meant as a definition that the properties of the support material do allow adhesion of the lipid layer that is supposed to be supported by the support layer. Additionally, it should be pointed out that already the support layer may have chemical and topographical properties that promote the fusion of the lipid layer on the support layer.

In order to improve or induce the formation and/or fusion and/or immobilization of the fluid lipid bilayers on the support layer to a desired extent, the surface of the support layer may be modified resulting in a promotion layer, i.e. using chemically activated hydrophobic or hydrophilic silanes or other components as well as modifications of physical nature such as topographical or electric modifications. This promotion layer may be designed according to the properties of the lipid bilayer to be supported and according to the mechanism responsible for the formation of the lipid bilayer.

With respect to the stability and to the free diffusion of macromolecules the thickness of the support layer in the nanopore array sections and the diameter of the nanopores may be chosen in order to result with an aspect ratio in the range of 0.25 to 5. In general, one nanopore array section comprises nanopores each having a diameter in the range of 50 to 2000 nm, preferably 100 to 2000 nm and the nanopore array sections have a thickness in the range of 50 to 2000 nm. The area of the nanopore array sections have an area in the range of $1 \times 10^{-6}$ mm$^2$ to 1 mm$^2$. For example, a pore diameter of 200 nm requires the support layer to be 400 nm thick for matching an aspect ratio of 2. Preferably, the aspect ratio may be in the range of 0.75 to 2. Thereby, very well suited pore diameters may range within an interval of 100 to 400 nm. This size offers an excellent compromise between the mechanical stability of the support layer and the biologically effective layer as well as it preserves the fluidity of the liquid bilayer membrane and the full functionality of the integrated membrane proteins. Further, the number of membrane proteins required for current macroscopic detection methods is limited to an economically reasonable extent.

With respect to achieve an efficient area of biological effective layer that meets a proper relationship between the area of the free standing lipid bilayer membranes in the nanopores and the supported lipid bilayer membrane area, said pores having a distance from each other in the range of 0.5 to 5-times, preferably 0.8 to 2-times of their diameter.

In practise, the biological effective layer may be isolated from a natural source which essentially are prokaryotic or eukaryotic cells as well as be a lipid bilayer prepared from lipid vesicles and later fusion of them.

The lipid component for the reconstituted bilayer can be selected from a group containing a phospholipid, a cardiolipid, a lysophospholipid, a ceramide, a ganglioside, a cerebroside, a glycolipid, a steroid, and a sphingolipid.

The biological effective layer comprise at least one non-lipid and/or functional molecule, whereby the non-lipid molecule can be selected from a group containing a protein, a polypeptide, a peptide or a synthetic compound (for instance with a biomimetic function); the protein can be an enzyme, a transport protein, a structural protein, a receptor, a cytokine, a hormome, a toxin, an inhibitor or a chaperone. These non-lipid molecules may be isolated or purified from a natural source like cells of eukaryotes or prokaryotes. Furthermore, the non-lipid molecule may be a synthetic compound.

The biological effective layer comprise at least one non-lipid and/or functional molecule, whereby the functional molecule may be from artificial origin like recombinant DNA or RNA technologies.

The biological effective layer may be formed with at least one intact living cell. Depending on the actual geometry of the nanopore array more than one cell may be used. The cells can be embedded into a biological effective layer which was deposited onto the nanopore array beforehand. If no such layer has been deposited the cells represent the biological effective layer on their own.

A suitable procedure for the investigation of the functionality of non-lipid molecules or functional molecule, being integrated in a biological effective layer in such an assay chip, according to the invention, comprises the steps of:

a) applying a fluid containing a molecule to one side of the fluid biological effective layer in order to allow the binding of the molecule to interact with the non-lipid molecule;

b) monitoring the response of the non-lipid molecule induced by effector binding and/or the interacting of binding molecules in the fluid biological effective layer by measuring physical or chemical changes on the cis- or trans-side of the assay chip.

Therefore, the above-mentioned assay chip can be used according to the invention in a drug discovery process with respect of the full functionality of membrane proteins in response to potential drug compounds to be screened. The binding can either be obeserved at the cis-side of the biological effective layer as e.g. fluorescence quenching or at the trans-side measuring changes in pH, $K^+$, $Na^+$ concentrations, measuring radioactivity or dyes in small volumes.

BRIEF DESCRIPTION OF THE SEVERAL VIEWS OF THE DRAWINGS

The following description will explain some of the preferred embodiments not limiting the invention and will quote the following drawings that are used to illustrate the present invention. Therefore, a brief description of the drawing is given below.

DETAILED DESCRIPTION OF THE INVENTION

Figure 1:
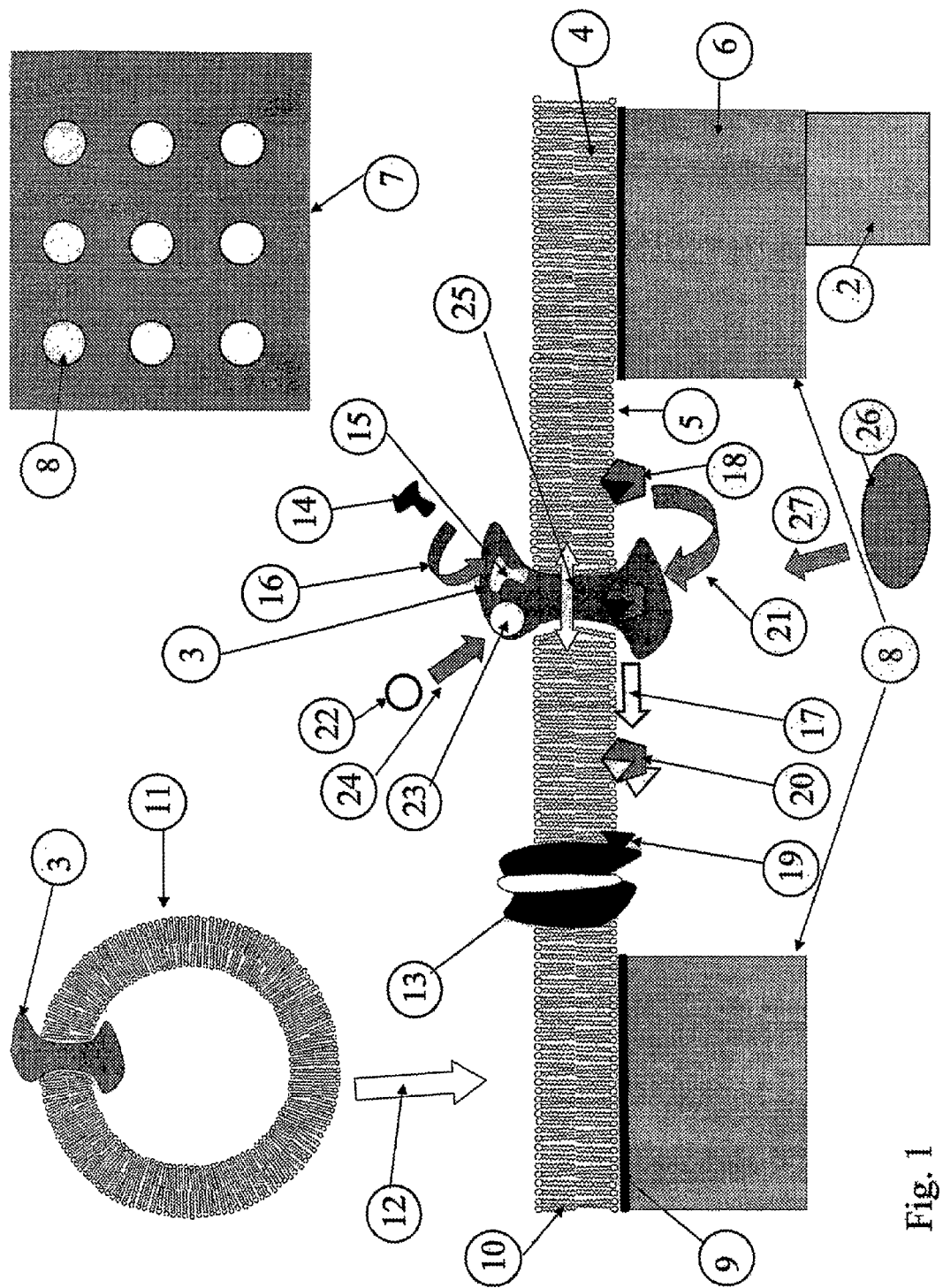
FIG. 1 is a schematic view of the biological mechanisms occurring in fluid lipid bilayer
Figure 2:
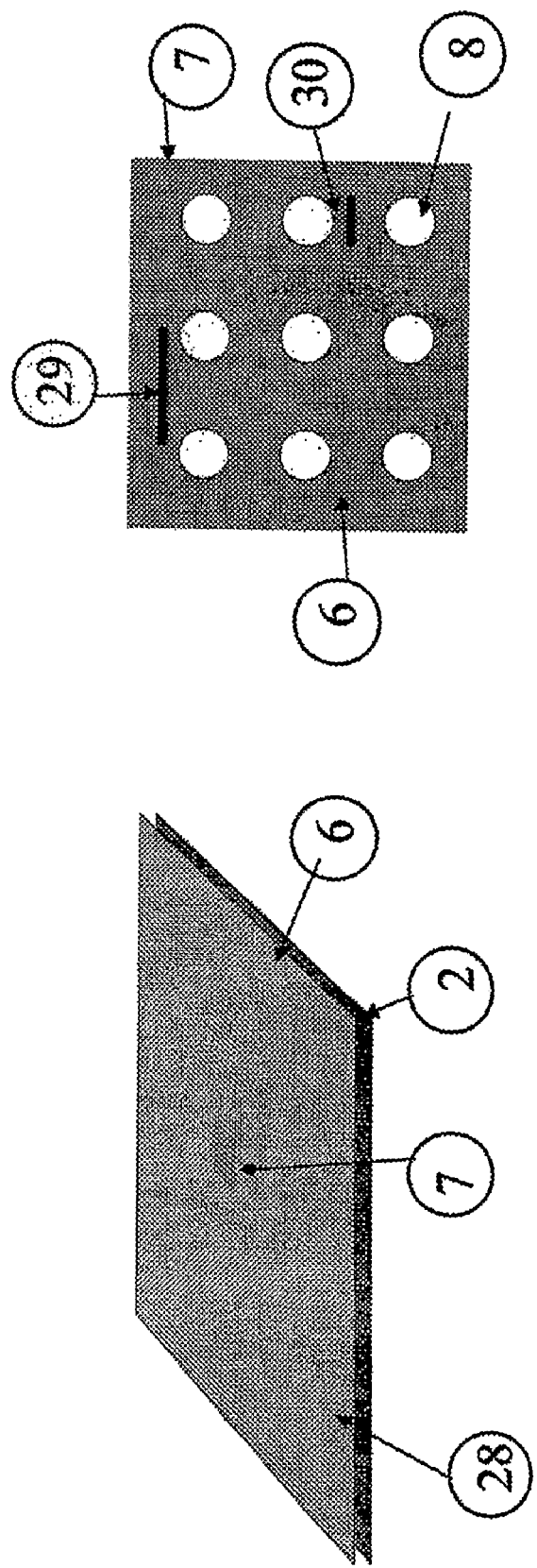
FIG. 2 is a schematic view on the design of a assay chip with a nanopore array and its dimension in a distinct embodiment according to the invention.

According to FIGS. 1 and 2, a portion of an assay chip 2 is shown to illustrate the biological function of a membrane protein 3. This assay chip 2 is the essential pre-requisite for the investigation of binding activities of the membrane proteins 3 which now combines both, the advantages of the supported 4 and of the free standing lipid bilayer membrane 5 as discussed above. The assay chip 2 comprises an array substrate 28 and a 300 nm thick silicon nitride layer 6 having sections in form of arrays 7 of pores 8 of diameters in the range of 50 nm and 2 μm. This supporting silicon nitride layer 6 is chemically modified with a support promotion layer 9 using activated hydrophobic silanes. The planar lipid bilayer membrane 4 on the surface of the supporting layer 6 or the support promotion layer 9, respectively, can be formed in various ways. In this embodiment, the hydrophobic chains 10 of a lipid vesicles are interacting with the hydrophobic support promotion layer 9 forming spontaneously a bilayer 4. In a second step lipid vesicles 11 with integral membrane proteins 3 are added and interact with the immobilized lipid bilayer 4. Fusion 12 of the vesicles 11 adhering to the support promotion layer 9 and in the second step to the formed bilayer can occur spontaneously at suitable conditions. Otherwise, fusion will be induced using fusogens. The fusion process can be monitored using optical, fluorescence and scanning probe microscopy or electrochemical methods.

When a continuous lipid bilayer membrane 4 without defects is achieved with neat lipid vesicles 11, lipid bilayer membranes with commercially available $Na^+$ and $Ca^{++}$ ionophores can be investigated. In a second phase membrane proteins are investigated as specified below. Alternatively, solubilized membrane proteins 3 can be incorporated directly into the prepared lipid bilayer membrane 4 on the nanopore array sections 7. Membrane proteins 3 are expected to gather preferably in the free standing regions of the lipid bilayer 5 in the nanopores 8.

The proposed concept allows to prepare membrane proteins 3 in vesicle suspensions 11 in a first step and to add the vesicles to the prepared lipid bilayer membranes 4 in a second step 12. The resulting free standing lipid bilayer membrane 4 has a sufficiently high mechanical stability concomitant with a long-range fluidity which is required to achieve full functionality of trans-membrane protein preparations.

The assay chip 2 is used to investigate the functionality of trans-membrane proteins 3 like GPCRS and their interactions with further membrane proteins like ion channels 13. To illustrate the importance of a fluid lipid bilayer for membrane protein activity in general the function of GPCRs are outlined in details. After binding of the natural ligand 14 to its binding site 15 which shall be represented by arrow 16 the GPCR get an catalytic activity resulting in a dissociation 17 of the specific trimeric G-protein molecule 18 in a $\alpha$-19 and a $\beta\gamma$ 20 subunit when it is bound to this membrane protein 3 (arrow 21) on the other side of the lipid bilayer membrane 4. The subunits 19 and 20 of the G-proteins 18 are covalently coupled via a lipid anchor to the lipid bilayer membrane 4 and can laterally diffuse within the lipid bilayer membrane 4 to the target membrane protein 13. Additionally, the effect of docking an allosteric effector molecule 22 to an allosteric site 23 of the membrane protein 3 (represented by arrow 24) can be monitored on its effect modulating the receptor function by way as an enhancer, agonist and antagonist. The induced structural changes in the membrane protein 13 result in a varity of biochemical reactions such as phosphorylation, c-AMP generation as depending on the type of the $\alpha$-subunit 19. In this specific embodiment the target protein 13 is an ion channel and transport of $K^+$-ions with high specificity through the lipid bilayer 4 will occur which is monitored as fluorescence of a potent $K^+$-specific crown ether indicator.

In this embodiment, the nanopore has a width of about 140 nm that makes it clear to the person skilled in the art that the membrane protein 3 is illustrated tremendously enlarged which allows the exemplarily description of the biological mechanisms. By an arrow 25 shall be indicated that the membrane protein 3 retains its flexibility in moving along the lipid bilayer 4 within the free standing pore region 5. In reality the membrane proteins 3 have a size of only a few nm that means that a number of a few membrane proteins 3 will be hosted in the same pore region allowing an average free lateral movement in the range of a large multiple of its dimensions. The aspect ratio which shall be in this example in the range of 1 thereby enables even larger molecules 26 to diffuse un-impeded (arrow 27) into the free standing pore region 5 and actually arrive at the receptor sites of the membrane protein 3 integrated in the lipid bilayer 4.

FIG. 2 depicts in a schematic way the design of a assay chip 2 which comprises in this embodiment an assay substrate 28 of 100 mm$^2$ total area having a 300 nm thin silicon nitride layer 6 with the actual nanopore array 7. The size of the silicon nitride membrane section 29 having the actual nanopore arrays 7 is about 1 mm$^2$. A nanopore array section 7 of 400×400 µm comprises nanopores 8 having diameters in the range of 50 to 2000 nm (indicated at 30). The distance of the nanopores 8 to each other (the pitch) is chosen to be in the range of their diameter 30. This guarantees both a sufficient stability of the lipid bilayer 4 on the suitable support layer 6 and a comparably high molecule density of membrane proteins 3 and the compounds (14, 22) to be screened diminishing utterly the amount of membrane proteins 3 and the compounds to be screened as well. To support this argument, a simple estimation is given below: Nanopores are disposed over an area of 400×400 µm corresponds to 0.16 mm$^2$ having a diameter of 125 nm and the same distance to each other. That leads to 2×10$^6$ pores on said area. Assuming that in each nanopore 8 a number of 10 membrane proteins molecules 3 of about 5 nm diameter will be hosted leads to a total amount of 2×10$^7$ membrane protein molecules or 3 10$^{-17}$ mol and a low filling factor of 0.2%. Depending on the molecular weight of the respective membrane molecule, assuming a molecule having a molecular weight of 30 kD, the required amount of the respective molecule is in the range of 1 pg per assay chip. An individual ion channel give a current of about 1 pA which correspondes to 10$^7$ ions/sec. The turnover of all ion channels in 100 sec will be about 10$^{-7}$ mol ions in an estimated liquid volume of about 10 µl which corresponds to a concentration of about 1 millimolar. The activity of many other membrane proteins will be lower, but the concentration of the compound to be detected in the mentioned small volume will be in the range of milli- to micromolar. This estimation apparently discloses that very tiny amounts of the respective molecules are required by using this assay chip design thereby the quantity is still sufficient to monitor concentration changes by detection methods on a macroscopic level, such as fluorescence and impedance. These tiny amounts of the respective molecules to be analysed towards its functionality and reaction on or as a natural ligand binding molecule and/or an allosteric effector molecule let the vision to appear realistic that this assay chip is absolutely the currently best choice for any type of drug discovery or screening process.

Figure 3:
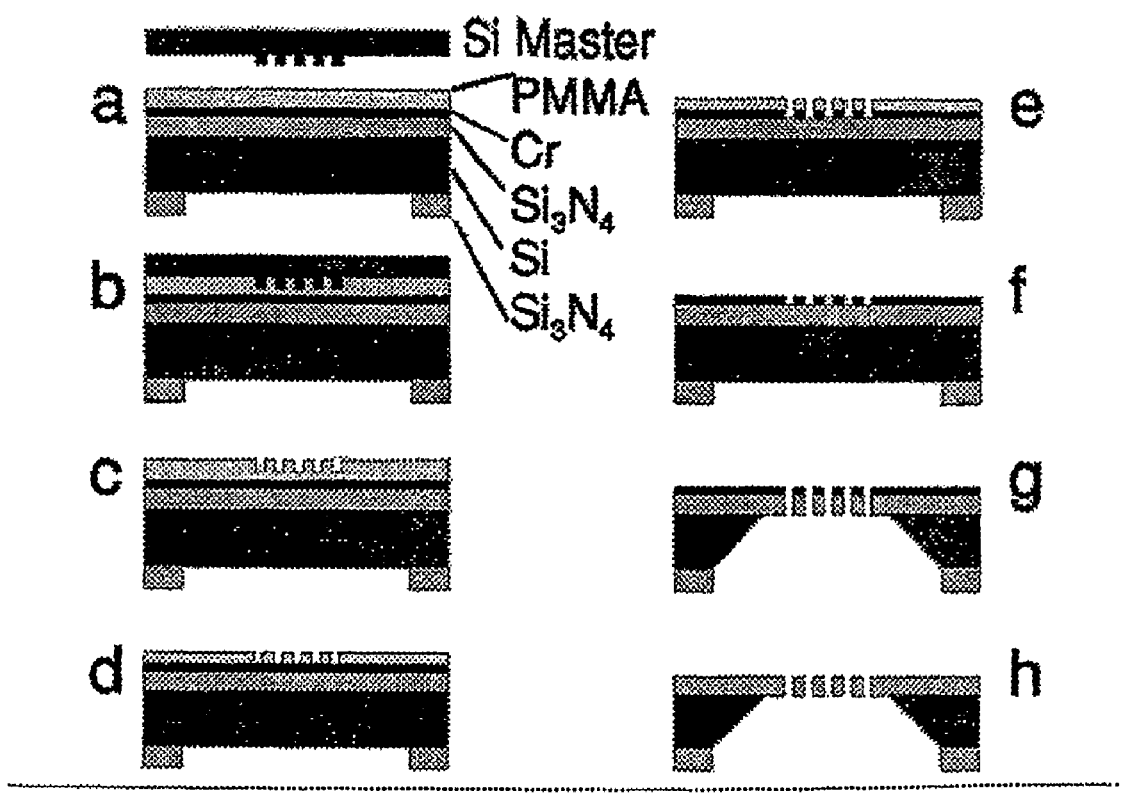
FIG. 3 is a schematic view on the manufacturing process of a assay chip with a nanopore array according to an embodiment of the invention.
Figure 4:
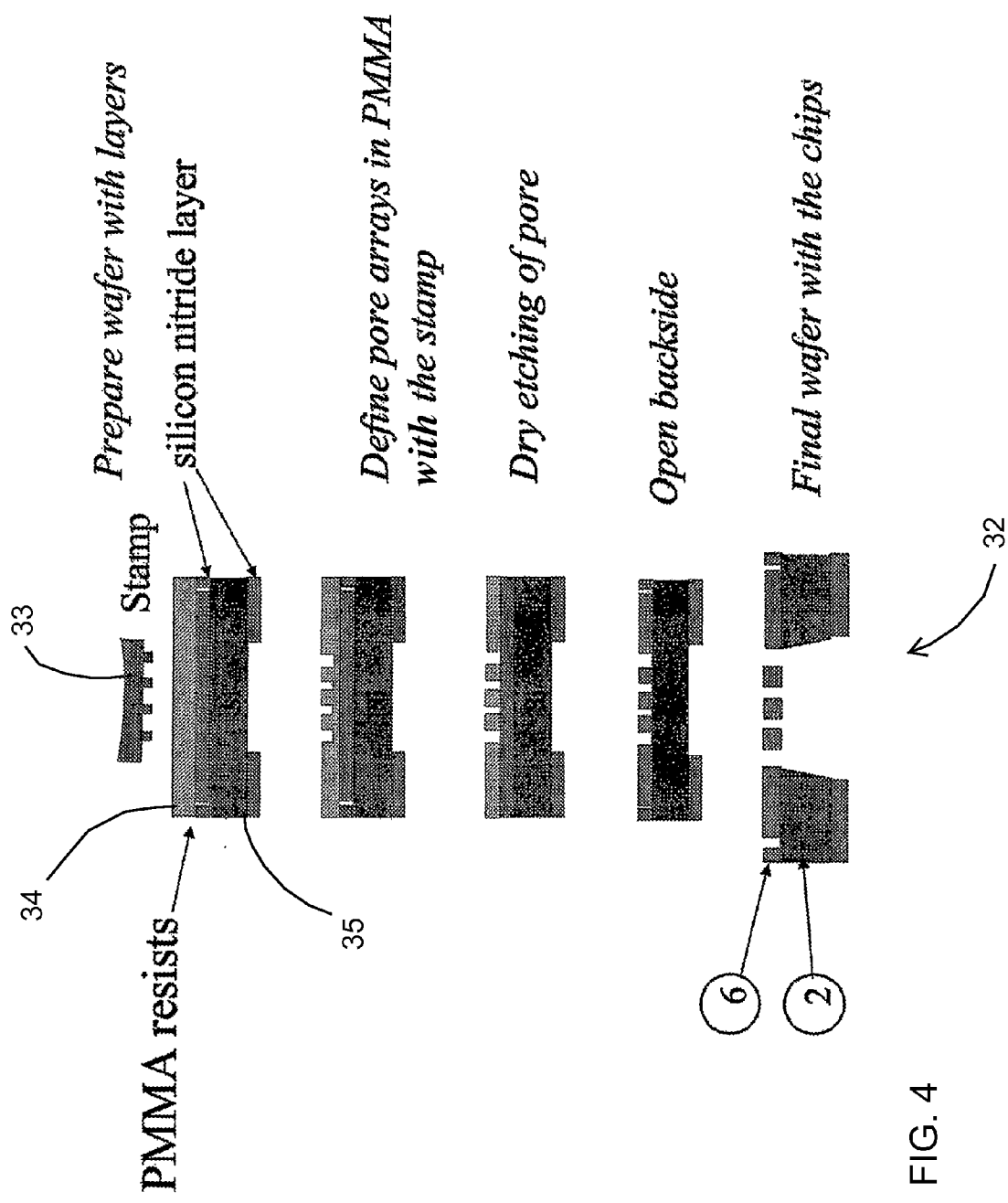
FIG. 4 is a schematic view of the production steps.

FIG. 3 schematically shows a process for manufacturing the nanopores in order to achieve a chip 32 comprising the substrate 28 and the support layer 6 with the nanopores 8, as set forth in FIG. 2. First, the nanopores 8 are replicated by hot embossing technique: As seen in FIG. 4, a stamp 33 is pressed into PMMA 34 (molecular weight 25 kg/mol) spin-coated to a thickness of 330 nm on a Si$_3$N$_4$ (260 nm)/Si (300 to 360 µm)/ Si$_3$N$_4$ (260 nm)/Cr (40 nm) substrate 35. A silicon master (square silicon pieces with side length 13.5 mm to be used as an embossing stamp) were fabricated with a Leica LION-LV1 electron beam writer using a scanned electron beam to write pore arrays in PMMA resists 34. Here the pore diameter is defined by the aperture size and the defocus of the electron beam, and the pore period is defined by the scanning step size. The final steps of the master fabrication include Cr lift-off to produce a dot array mask and them RIE of silicon dioxide to produce pillar arrays in the stamp with a height of 130 nm. The Si$_3$N$_4$ on the reverse side of the substrate is pre-structured with square openings (side length: 1×1 mm) to be used as a mask for the final Si$_3$N$_4$-membrane production step (FIG. 3B). The Si$_3$N$_4$-layer on the front side of the substrate includes alignment marks (13.5×13.5 mm frame) to align the embossing master so that the nanopores coincide with the Si$_3$N$_4$-membranes, and break lines (10×10 mm frame) for removal of the final 10×10 mm chip form the wafer which allows improved handling. Following embossing, PMMA residual layer is removed using an O$_2$ plasma and the pores transferred into the Cr layer with a Cl$_2$/CO$_2$ plasma (FIG. 3C). The PMMA mask is then removed with O$_2$ plasma before transferring the pores into the Si$_3$N$_4$ with a CHF$_3$/O$_2$ plasma. The Si is etched with a KOH bath at 70° C. to open the backside of the silicon nitride membranes (FIG. 3D) and the Cr mask is removed with Cl$_2$/CO$_2$ etch to give the final chip (FIG. 3E).

The invention claimed is:

1. An assay chip for investigation of a functionality of non-lipid molecules and their interactions with molecules, comprising:
   a nanopore substrate having a plurality of nanopores and alignment marks, said nanopore substrate having a thickness and said nonapores having a diameter in a range of 50 to 2000 nm resulting in an aspect ratio in a range of 0.5 to 2;
   b) a substantially planar support layer deposited on said nanopore substrate and having a plurality of nanopores corresponding to and aligned with said nanopores of said nanopore substrate;
   c) a biologically effective layer configured to host at least one of a non-lipid molecule and functional molecule, deposited on said support layer and covering the plurality of nanopores, resulting in accessible nanopores from both sides of the biologically effective layer for measurements, wherein the biologically effective layer is a biomembrane isolated from one of prokaryotic and eukaryotic cells, wherein the biologically effective layer is a lipid bilayer formed by preparation and later fusion of lipid vesicles or is a functional layer of supramolecular assembly, and said biologically effective layer retaining biological functionality.

2. The assay chip according to claim 1, wherein a surface of the support layer is chemically modified by at least one of activated hydrophobic and hydrophilic silanes resulting in a support promotion layer.

3. The assay chip according to claim 1, wherein the support layer is selected from the group consisting of silicon nitride ($Si_3N_4$) and silicon oxide substrate, and wherein the substrate is selected from the group consisting of silicon and carbon containing materials, polymers, metals, dielectrica, glass and ceramics.

4. The assay chip according to claim 1, wherein said nanopores are arranged in a plurality of nanopore array sections having an area in the range of $1\times10^{-6}$ $mm^2$ to 1 $mm^2$ on a total free standing silicon nitride membrane area of $1\times10^{-6}$ $mm^2$ to 10 $mm^2$.

5. The assay chip according to claim 1, wherein said nanopores have a distance from each other in the range of 0.5 to 5-times of their diameter.

6. The assay chip according to claim 5, wherein said nanopores have a distance from each other in the range of 0.8 to 2-times of their diameter.

7. The assay chip according to claim 1, wherein the non-lipid molecules are from a natural source selected from the group consisting of eukaryotes and prokaryotes.

8. The assay chip according to claim 1, wherein the biologically effective layer hosts a non-lipid molecule, and wherein the non-lipid molecule is a synthetic compound.

9. The assay chip according to claim 1, wherein the biomembrane and the lipid bilayer each comprise at least one of a non-lipid and functional molecule, whereby the functional molecule is produced using one of recombinant DNA and RNA technologies.

10. The assay chip according to claim 1, wherein the biologically effective layer is made from at least one intact living cell.

11. The assay chip according to claim 1, wherein the diameter of the nanopores is chosen in order to result with an aspect ratio in the range of 0.75 to 2.

12. The assay chip according to claim 1, wherein the diameter of the nanopores is in the range of 100 to 2000 nm.

13. A process for analyzing a functionality of at least one of a non-lipid molecule and functional molecule being integrated in a biologically effective layer of an assay chip of claim 1, and a biologically effective layer the process, comprising:
   applying a fluid containing a binding compound to one side of the biologically effective layer in order to allow binding compound to interact with the non-lipid molecule;
   monitoring the response of the non-lipid molecule induced by at least one effector binding and an interaction of binding molecules in the biologically effective layer by measuring physical or chemical changes on cis- or trans-sides of the assay chip.

* * * * *